(12) United States Patent
Masuo

(10) Patent No.: US 6,243,651 B1
(45) Date of Patent: *Jun. 5, 2001

(54) HEALTHCARE DATA ACQUISITION DEVICE

(75) Inventor: Yoshihisa Masuo, Kyoto-fu (JP)

(73) Assignee: Omron Corporation, Kyoto (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/992,228

(22) Filed: Dec. 17, 1997

(30) Foreign Application Priority Data

Dec. 17, 1996 (JP) .................................................. 8-354027
Dec. 17, 1996 (JP) .................................................. 8-354039

(51) Int. Cl.$^7$ ........................................................ A61B 5/05
(52) U.S. Cl. ............................................. 702/19; 600/547
(58) Field of Search .............................. 702/19, 57, 182; 600/382, 547, 554, 587

(56) References Cited

U.S. PATENT DOCUMENTS 4,895,163 * 1/1990 Libke et al. ......................... 600/547
4,911,175 * 3/1990 Shizgal ............................... 600/547
5,449,000 * 9/1995 Libke et al. ......................... 600/547
5,579,782 * 12/1996 Masuo ................................ 600/547
5,611,351 * 3/1997 Sato et al. .......................... 600/547
5,720,296 * 2/1998 Cha ................................... 600/554

* cited by examiner

Primary Examiner—Kamini Shah
Assistant Examiner—Bryan Bui
(74) Attorney, Agent, or Firm—Morrison & Foerster LLP

(57) ABSTRACT

A conventional healthcare data acquisition device for advising on various healthcare data currently exists by measuring an impedance across a patient body. To measure the impedance of the patient in the conventional device, the patient grips a pair of current electrodes and measurement electrodes by both palms. The conventional device, however, is not accurate because the resistance value becomes very large due to the presence of the joints and the small diameter of the fingers. Moreover, the adjacent fingers may at different times be apart or in contact with each other, thus resulting in a varying current path. The invention overcomes these problems by providing a healthcare data acquisition device having a pair of current electrodes to contact specifically left and right thumbs of a user in order to apply a stable current, and a pair of measurement electrodes to contact a pair of specified portions which are respectively located between the left and right thumbs and wrists of the user so that stable impedance and voltage can be measured.

8 Claims, 14 Drawing Sheets

HEALTHCARE DATA ACQUISITION DEVICE

FIELD OF THE INVENTION

The present invention generally relates to healthcare management devices and, more particularly, to a healthcare data acquisition device which measures the impedance of the body and, based on the value obtained, provides various data which are useful with respect to healthcare management.

BACKGROUND OF THE INVENTION

A healthcare data acquisition device belonging of the prior art is shown in FIG. 16. On either side of device 200 are grips 205 and 206. In the two grips 205 and 206 are cylindrical current electrodes 201 and 202, respectively, which apply a current to a patient using the device. The two grips 205 and 206 further include measurement electrodes 203 and 204, respectively, which measure voltage across the body of the patient.

Prior to measurement, the patient uses input unit 210 to enter physical characteristics, for example, data such as height, weight, age and sex. To measure the impedance of the body, the patient holds grips 205 and 206 with both hands so that current electrodes 201 and 202 are in contact with the parts of the hands between the thumbs and the index fingers, and measurement electrodes 203 and 204 are in contact with the palms of the hands below the fourth and fifth fingers. By measuring the potential developed across the body due to its resistance with respect to the current which is applied, the impedance of the body can be obtained. The general relationship between the impedance of the body and data relating to healthcare such as percentage of body fat is stored in a data base obtained by statistical methods. Using this data base and the measured impedance of the body, data are obtained which can be useful in managing the healthcare of the patient.

With the electrode configuration of device 200, it was possible in the prior art to produce a small, light and inexpensive healthcare data acquisition device which could measure impedance with accuracy and repeatability as compared with the method shown in FIG. 17. In FIG. 17, a current electrode 207 is attached to the back of the hand at the base of the index and middle fingers, and a measurement electrode 208 is attached to the top of the wrist. These electrodes are then connected to a healthcare data acquisition device (not shown) for measuring an impedance of the patient. The healthcare data acquisition device as used in the method of FIG. 17, however, is typically bulky and hard to operate. Accordingly, despite the improvements in the art of providing a smaller, lighter and less expensive healthcare data acquisition device such as device 200, there remains an opportunity to make the device even smaller, lighter and cheaper.

Attempts have been made to reduce the size of the electrode structure by using electrodes in contact with the fingertips. This design, however, results in inferior accuracy and repeatability. When the electrodes for applying the current are attached to the fingertips, the resistance value becomes extremely large due to the presence of the joints and the small diameter of the fingers. This results in errors due to difficulty in maintaining a constant current source. Adjacent fingers may at different times be apart or in contact with each other, thereby resulting in a varying current path. As a result, this adversely affects the repeatability and stability of the measurement. As to the prior art method of FIG. 17, the further apart the electrodes are from the measurement device, or the further apart they are from the main current path, the more likely it is that measurement errors and inconsistencies will occur.

SUMMARY OF THE INVENTION

A feature of this invention is to reduce the size of the electrode structure of a healthcare data acquisition device in order to make the device even smaller, lighter and cheaper.

The present invention was developed to address the aforementioned problems in the existing technology by providing a smaller, lighter and cheaper healthcare data acquisition device which provides highly accurate and repeatable measurements.

In order to provide the feature mentioned above, a first embodiment of this invention is a healthcare data acquisition device with two electrodes which apply a current from a specified part of the body and two electrodes which measure the voltage generated in that part of the body by the current. The impedance of the body is measured using the current and voltage. Based on the measured impedance of the body, data are provided which are useful in healthcare management. This invention is distinguished from the prior art in that the only body parts to which current is applied are the patient's thumbs.

By the phrase "body parts to which current is applied" is meant those parts of the body which must be in contact with the electrodes which apply current.

By applying current only to the thumbs, which are the thickest digits and so have a low resistance value, errors relating to the constant current source are minimized, and a highly accurate impedance measurement may be achieved.

Moreover, since the thumbs are independent both structurally and functionally from the other four fingers, applying current only to the thumbs eliminates the possibility that the current path will vary. It is then possible to measure the impedance with good accuracy and repeatability.

The area of the skin where the current electrodes make contact with the thumbs is large enough to allow the use of smaller electrodes. This in turn allows the entire device to be made smaller, lighter and cheaper.

If the current to be applied to the pads is only going to the thumbs, then the electrodes can be installed on the surface of the device. The patient then need only place the thumbs on them or grasp them, and the impedance can be easily measured.

A second embodiment of this invention has a configuration identical to the first invention, except that it has position guides to insure that the thumbs make contact with the current electrodes. These position guides help the specified parts of the thumbs make proper contact with the current electrodes, thus providing a healthcare data acquisition device capable of a high degree of accuracy and repeatability.

The thumbs can also be positioned correctly by using current electrodes which are designed so as to maintain contact with the specified parts of the thumbs. Another alternative is to provide a structural component along the periphery of each electrode to limit the movement of the thumb and guide its placement.

A third embodiment is distinguished in that the current electrodes in either the first or the second embodiment are shaped to correspond to the thumbs. This third embodiment makes it easier to position the specified portions of the thumbs on the current electrodes. It thus makes it possible to provide a healthcare data acquisition device capable of high accuracy and repeatability.

The current electrodes may be three-dimensional and conform to the contours of the specified portions of the thumbs, or they may be flat but shaped in such a way that the user can confirm that the thumbs are in contact with the electrodes.

A fourth embodiment of this invention is distinguished in that in the first through third embodiments, the portion of each hand between the base of the thumb and the wrist is selected as the site where the voltage will be measured. The term "site where the voltage will be measured" refers to the portion of the body where the electrodes to measure voltage must be in contact with the skin. Although the thumbs are selected as the sites where the current is to be applied, they are not far from where the electrodes were attached in the prior art measurement method. The deviation of the current from the main current path is also slight, so the problems of measurement error and the incongruity of the measurement method with respect to the prior art method are minimized. A healthcare data acquisition device can thus be produced which is capable of highly accurate measurements. Because the current and measurement electrodes can be placed quite close to each other, this allows the device to be made smaller, lighter and cheaper. If the voltage is measured between the base of the thumb and the wrist on each hand, then the impedance can be easily measured if the patient places the hands on or grasps the measurement electrodes which are installed on the surface of the device.

A fifth embodiment of this invention is distinguished from embodiments 1 through 4, in that the impedance measurement begins while the current and measurement electrodes and the specified parts of the body which must be in contact with those electrodes are maintained in a state of contact which allows the impedance to be measured. By "a state of contact which allows the impedance to be measured" is meant the state such that the specified parts of the body directly touch the parts of the device which correspond to the electrodes to apply current and those to measure voltage. With this design, the specified parts of the body are placed in contact with the current and measurement electrodes and preparations are made to perform the measurement. The measurement then begins without any change in the state of contact. There is no danger of the sort of measurement error which might occur if there were, for example, a switch in a separate location which must be actuated to begin the measurement, so that the measurement might be performed with the fingers in the wrong position. This design insures a highly accurate measurement.

A sixth embodiment of this invention is distinguished from the fifth embodiment in that a portion of at least one of the current electrodes is cut away and a start switch is provided in the cut-away portion. In this embodiment, preparations for the measurement are completed while the specified body parts are in contact with the current electrodes. The patient can actuate the start switch without breaking contact with the electrodes. This prevents the sort of measurement errors which are associated with initiating the measurement operation and so insures that a highly accurate measurement can be made.

A seventh embodiment of this invention is distinguished from the fifth embodiment in that the start switch is integral to at least one of the current electrodes. In this embodiment, preparations for the measurement are completed while the specified body parts are in contact with the current electrodes. The patient can actuate the start switch without breaking contact with the electrodes. This prevents the sort of measurement errors which are associated with initiating the measurement operation and so insures that a highly accurate measurement can be made.

An eighth embodiment of this invention is distinguished from the fifth invention in that the judgment that the preparation for measurement has been completed is based on a determination that the current and measurement electrodes are in contact with the appropriate part of the body, and the measurement does not begin until the preparation has been completed. Thus when the current electrodes have been placed in contact with the specified part of the body and the preparation has been completed, no change in the state of contact is required to begin the measurement. This prevents the sort of measurement errors which are associated with initiating the measurement operation and so insures that a highly accurate measurement can be made.

DETAILED DESCRIPTION OF THE INVENTION

Figure 1A:
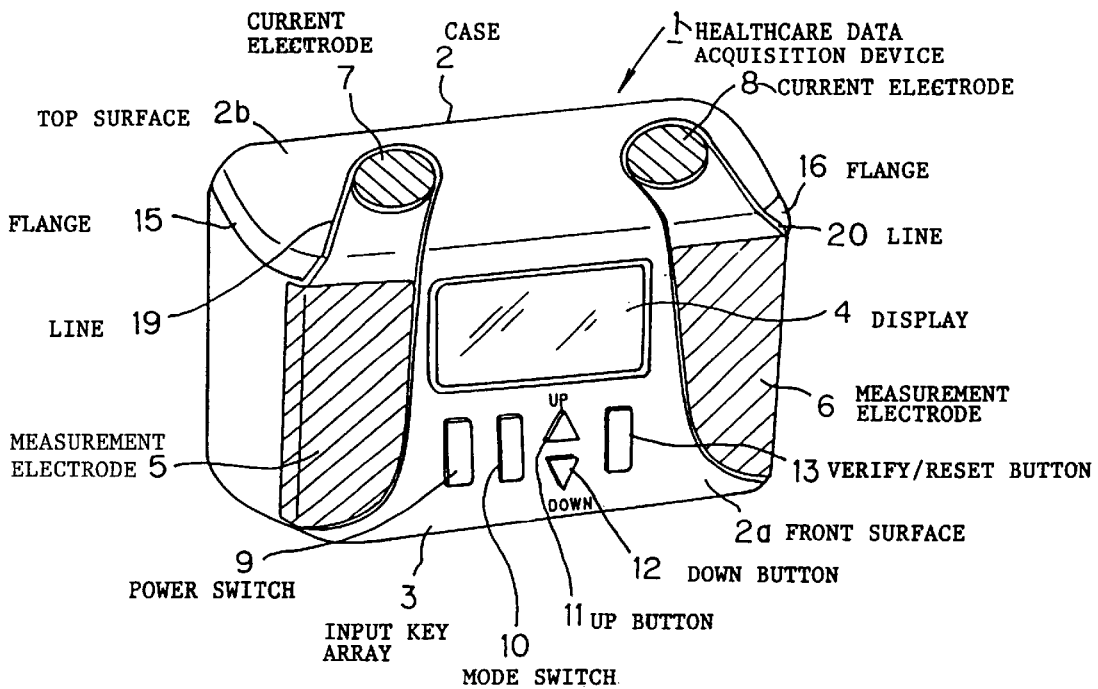
FIG. 1(a) is a perspective drawing of a healthcare data acquisition device in accordance with the first embodiment of this invention.
Figure 1B:
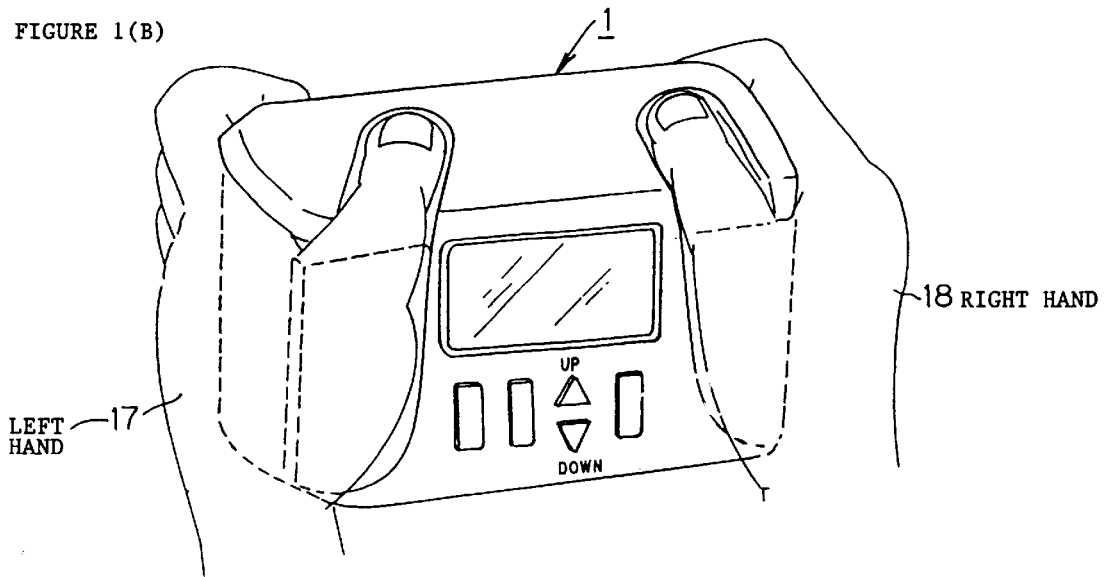
FIG. 1(b) illustrates the use of the healthcare data acquisition device in accordance with the first embodiment of this invention.

FIGS. 1(a) and 1(b) are rough sketches of the exterior of healthcare data acquisition device 1, the first embodiment of this invention. As can be seen in FIG. 1(a), case 2 of device 1 is a rectangular-shaped box. Its front surface 2a has an input key array 3 and a display 4. On either side of front surface 2a of device 1 are flat measurement electrodes 5 and 6. On either side of top surface 2b of device 1 are round- or oval-shaped current electrodes 7 and 8. Case 2 of device 1 is formed of a molded resin such as polycarbonate ABS or ABS.

Input key array 3, in the lower center portion of front surface 2a of device 1, includes power switch 9, mode switch 10, UP button 11, DOWN button 12 and verify/reset button 13. Mode switch 10 is used to select an input mode. UP and DOWN buttons 11 and 12 are used to move the numerical values which have been entered or displayed on display 4 in step fashion in the specified direction. Verify/reset button 13 is used to verify the input data or erase them so that new data can be entered.

Display 4 on the upper portion of front surface 2a of device 1 consists of an LED or LCD which displays various data in the form of numerals and letters.

Electrodes 5, 6, 7 and 8 may be formed of a Cr-plated resin, a Cr-plated sheet metal, an SUS plate or an SUS sheet, or some similar conductive material which is highly resistant to corrosion.

On the left and right ends of upper surface 2b of device 1 are flanges 15 and 16, which protrude slightly from the sides of the case 2.

Figure 2:
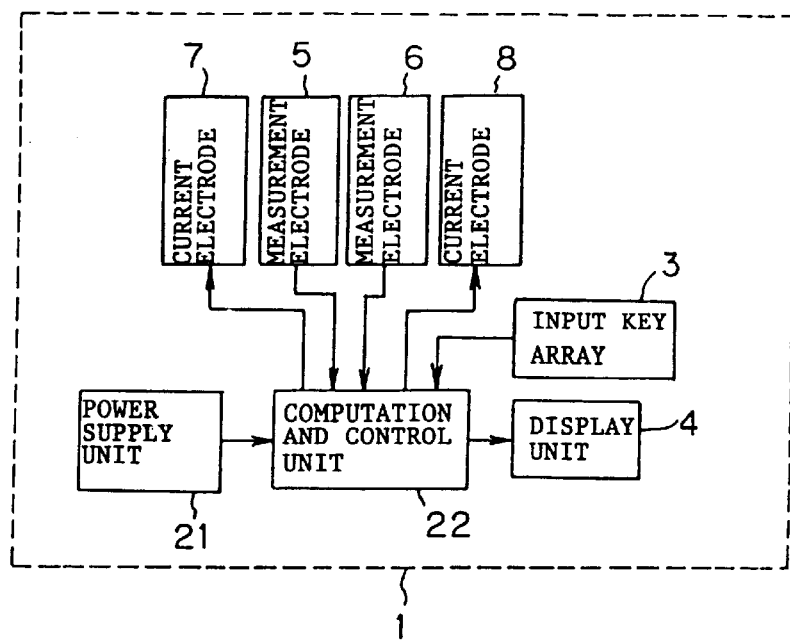
FIG. 2 is a block diagram showing the internal configuration of the healthcare data acquisition device in accordance with the first embodiment of this invention.

The order of operations performed by device 1 is now explained by reference to FIG. 2, a block diagram of the internal configuration of device 1.

First, a user, for example, a patient, actuates power switch 9. Power is then supplied from power supply unit 21 to the various parts of the device.

The user selects input mode via mode switch 10 and enters his personal data, for example, data such as height, weight, age and sex, using UP and DOWN buttons 10 and 11. If he has entered the data correctly, then he uses verify/reset button 13 to verify the data; if he has made an error, then he resets the display using button 13 and reenters the data.

Figure 3:
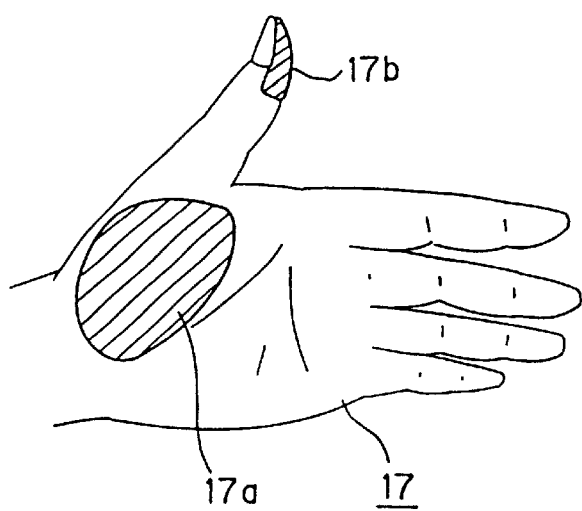
FIG. 3 shows the parts of the left hand which make contact with the electrodes in the healthcare data acquisition device in accordance with the first embodiment of this invention.

Once all the data have been entered, the user grasps the specified locations on the left and right sides of device 1 with his hands (17 and 18), as shown in FIG. 1(b). The portions of the hands where the base of the index finger meets the thumb run up against flanges 15 and 16 on the sides of device 1 so that the hands are kept in the proper position. At this point, as can be seen by reference to FIG. 3, the portion of the left palm 17a from the base of the thumb to the wrist is in contact with measurement electrode 5, and the pad of the thumb 17b is in contact with current electrode 7. Similarly, the portion between the base of the right thumb and the wrist and the pad of the right thumb are in contact with measurement electrode 6 and current electrode 8.

As FIG. 1(a) shows, measurement electrodes 5 and 6 and current electrodes 7 and 8 are shaped so as to correspond to the portions of the hands from the base of the index finger to the wrist and the pad of the thumb. Guidelines 19 and 20 around their edges make it easy for the user to position his hands correctly. As has been discussed previously, the correct placement of the hands enables a highly accurate and repeatable measurement. In this embodiment, the guidelines are made lower than the surface of the case, i.e., the edges of electrodes 5, 6, 7 and 8 are slightly incised. However, it would also be possible to raise the edges slightly or to outline the edges of the shapes in paint.

When the user has placed his hands in the specified positions, the preparation is completed. The user then actuates the start switch (not pictured) and the measurement is begun. When the start switch is actuated, a high-frequency current is applied to the pads of the thumbs by way of current electrodes 7 and 8. The resistance-dependent potential of the body from hand to hand which is generated by this current is captured by measurement electrodes 5 and 6.

The signal which is captured is picked up by computation and control unit 22 (see FIG. 2) and processed by a specified program to calculate the impedance. The measured impedance value and the personal data which were entered via key array 3 are operated on and processed according to a specified program. Various indices such as fat content, lean body mass, percentage of body fat, fluid content and basic metabolic rate are calculated. In addition, data which might be useful in managing the user's healthcare may be calculated based on these indices. The measured impedance value, the various indices such as fat content and the data to guide healthcare management appear on display 4.

Thus only the pads of the thumbs are in contact with current electrodes 7 and 8, and the current is applied only to the thumbs. Since the thumbs are relatively thick and have a low resistance value, they tend to minimize constant current errors. This enables a highly accurate measurement of impedance.

The thumbs can also be easily kept separate from the other fingers in terms of both structure and function. When the user grasps device 1 as shown in FIG. 1(b), his thumbs are easily and effectively separated from his fingers. There is no chance that his thumbs will come in contact with his other fingers during the measurement, causing the current path to fluctuate. As such, this insures a highly accurate and repeatable measurement.

If the thumbs are placed in contact with current electrodes 7 and 8 and the portions of the hands between the bases of the thumbs and the wrists are placed in contact with measurement electrodes 5 and 6, the positions of the electrodes will not be very far from those used in the prior art measurement method, and the deviation of the current from the main current path will not be large. Thus problems of measurement error with respect to the prior art method and inconsistencies of the measurement method will be minimized, and the impedance can be measured with great accuracy.

As can be seen in FIG. 1(a), current electrodes 7 and 8 need only be as large as the pads of the thumbs which must be in contact with them. This allows the healthcare data acquisition device to be made smaller, lighter and cheaper.

In this embodiment, the measurement electrodes are placed only on front surface 2a of device 1; however, it would also be possible to have them continue around the sides or even to the back of device 1.

The start switch may be placed in any suitable location; however, it is recommended that it be placed where a portion of current electrode 7 or 8 has been cut away or be formed integrally with either electrode 7 or electrode 8. It would also be acceptable for the measurement to begin automatically once the device detects that preparations have been completed by noting that the hands are in contact with current electrodes 7 and 8 and measurement electrodes 5 and 6. Any of these designs will prevent the sort of measurement error which occurs when the impedance is measured just after the user moves his thumb to actuate the start switch, so a highly accurate measurement is insured.

In this embodiment, current electrodes 7 and 8 are of a size to correspond to the pads of the thumbs. However, it would also be possible to make the current electrodes tongue-shaped, so that they extend from top surface 2b onto front surface 2a. This would extend the contacting portions of the thumbs from the pads down to the first or second joints.

Figure 4:
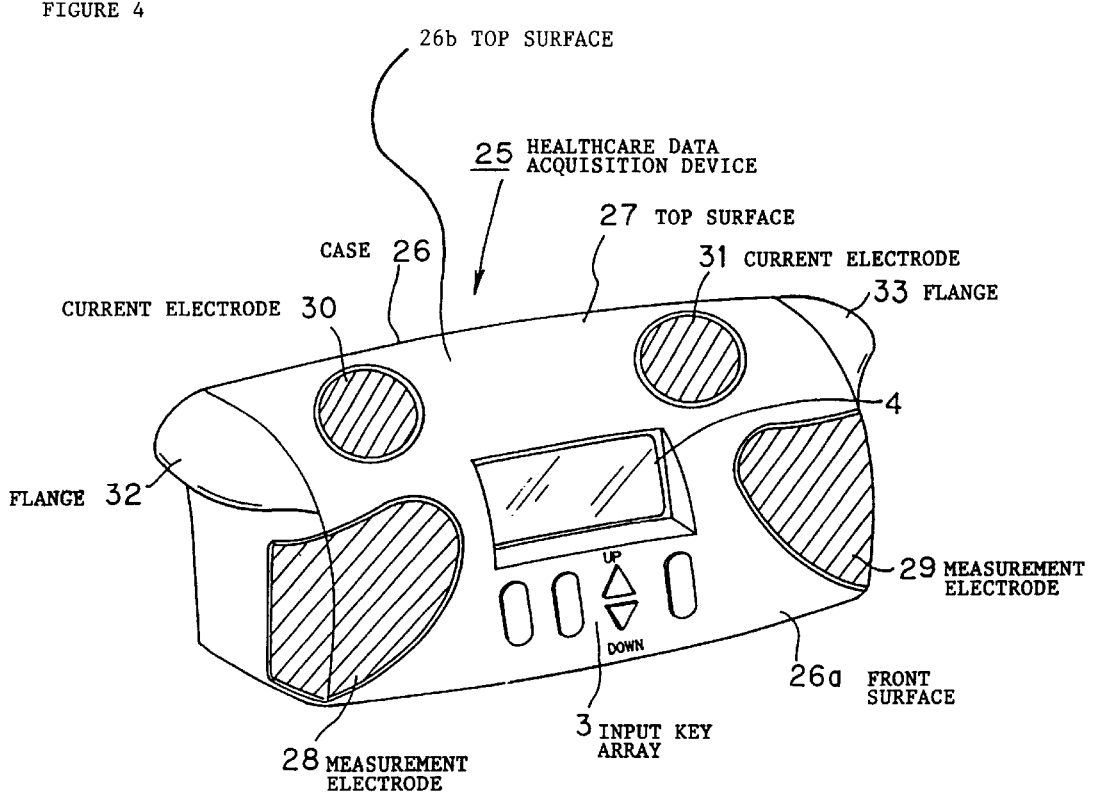
FIG. 4 is a perspective drawing of a healthcare data acquisition device in accordance with the second embodiment of this invention.

FIG. 4 shows healthcare data acquisition device 25, the second embodiment of this invention. Components which are configured just as in the first embodiment are given the same numbers. The order of operations and the internal configuration are also identical to those of the first embodiment.

In this embodiment, front surface 26a and top surface 26b of case 26 are connected to form a single downward-sloping curved surface. Display 4 and input key array 3 are in the lower portion of the middle of front surface 26a of device 25. On either side of the lower portion of front surface 26a of device 25 are tongue-shaped measurement electrodes 28 and 29. The ends of electrodes 28 and 29 are on the sides of device 25. Round-shaped current electrodes 30 and 31 are on either side on the top of front surface 26a of device 25. Tongue-shaped flanges 32 and 33 extend from either side on the upper edge of front surface 26a. From the edge of device 25, the upper surfaces of flanges 32 and 33 curve gently outward and down. The surface on either side of the upper portion of device 25 curves outward to meet the edges of flanges 32 and 33.

The user grasps the sides of device 25 from the front with both hands. The sides of the hands going toward the thumbs near the bases of his index fingers come up against the bottoms of flanges 32 and 33 to insure that they will be positioned properly. When the user extends the thumbs upward over the curving surface of the device, the portions of the palms between the bases of the index fingers and the wrists make contact with measurement electrodes 28 and 29, and the pads of the thumbs make contact with current electrodes 30 and 31. When the portions of the thumbs between the pads and the bases are extended along the curved surface of case 26, the positions of the thumbs are fixed. This insures that the impedance measurement will be accurate and repeatable.

The shapes of the current and measurement electrodes are not limited to those shown in the drawings.

FIG. 5 shows healthcare data acquisition device 35, the third embodiment of this invention. Aspects of the configuration which are identical to corresponding parts of the first embodiment are labeled with the same numbers. The order of operations and the internal configuration are also identical to those of the first embodiment.

Figure 5A:
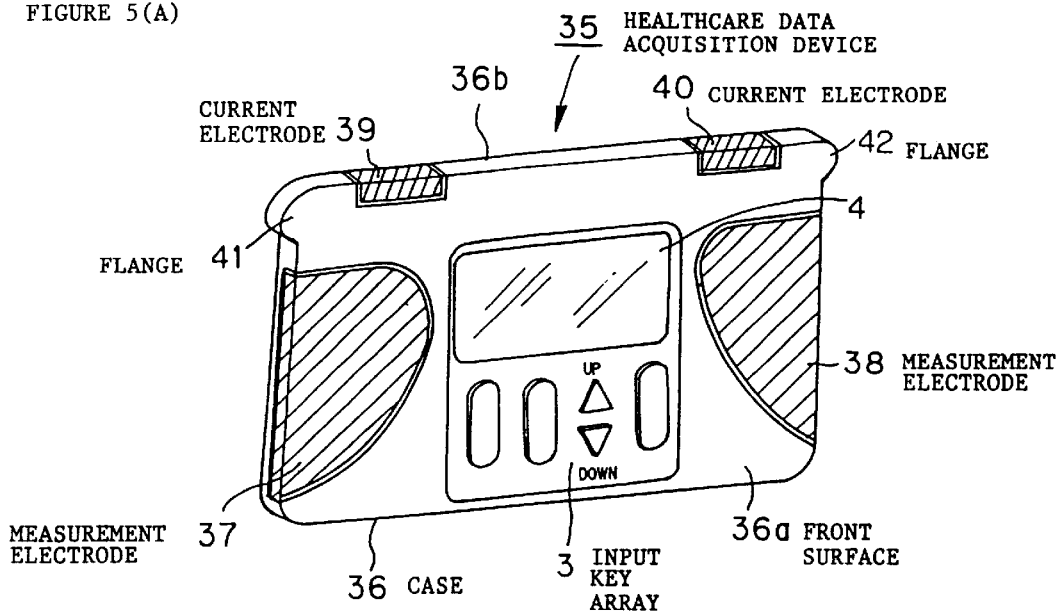
FIG. 5(a) is a perspective drawing of a healthcare data acquisition device in accordance with the third embodiment of this invention.

As is shown in FIG. 5(a), case 36 of device 35 has the form of a card. Input key array 3 and display 4 are in the center of front surface 36a of device 35. On either side of surface 36a are tongue-shaped measurement electrodes 37 and 38. The ends of electrodes 37 and 38 wrap slightly around the edges on either side of device 35. Rectangular current electrodes 39 and 40 are on either side of top surface 36b of device 35. Their ends wrap slightly around onto front surface 36a. The left and right edges of top surface 36b extend outward to form flanges 41 and 42. When the user grasps the sides of device 35, the part of each hand between the index finger and the thumb comes up against one of these flanges so as to position the hands properly.

Figure 5B:
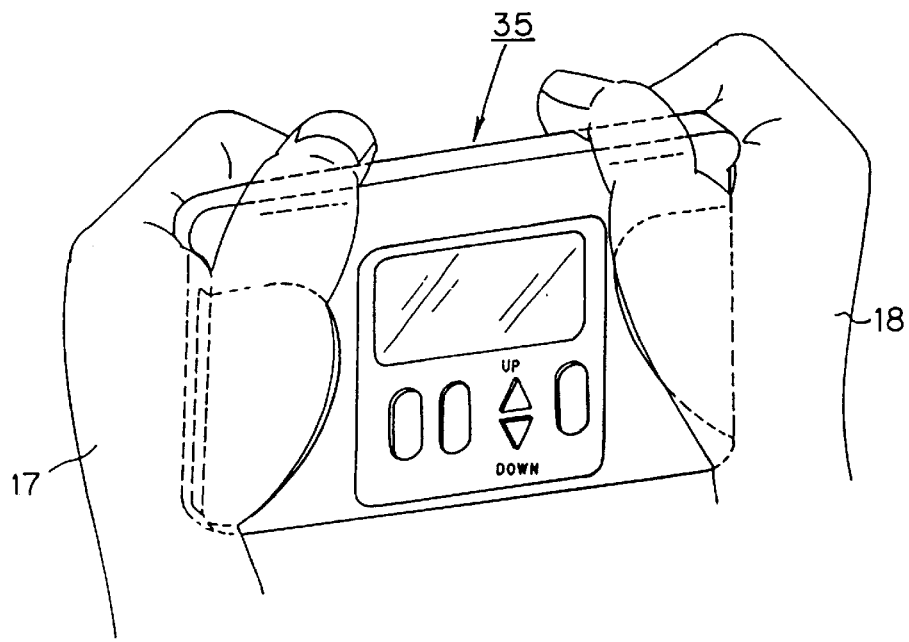
FIG. 5(b) illustrates the use of the healthcare data acquisition device in accordance with the third embodiment of this invention.

When the user grasps device 35 from the front with both hands, as can be seen in FIG. 5(b), the parts of the palms from the base of each index finger to the wrist come in contact with measurement electrodes 37 and 38, and the pads of the thumbs come in contact with current electrodes 39 and 40. The first joints of the thumbs are on the edge where front surface 36a meets top surface 36b. In this way the thumbs can be held in the proper position reliably to insure that the impedance measurement will be accurate and repeatable.

Figure 6:
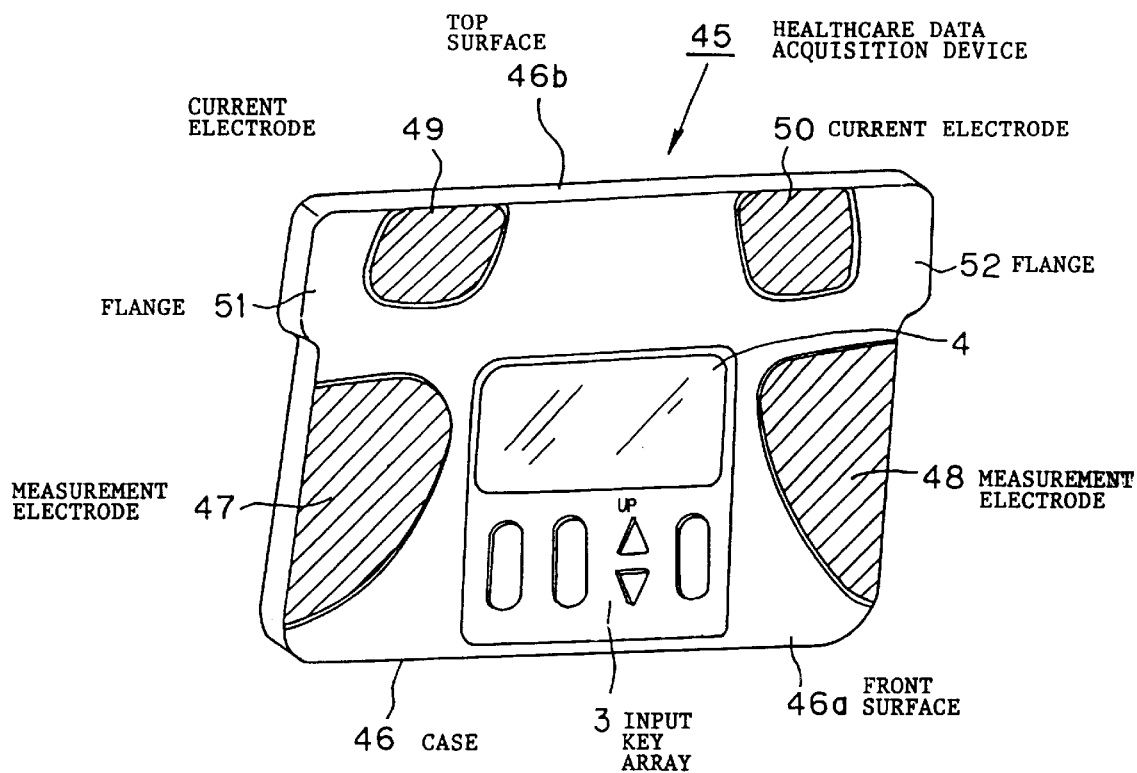
FIG. 6 is a perspective drawing of a healthcare data acquisition device in accordance with the fourth embodiment of this invention.

FIG. 6 shows healthcare data acquisition device 45, the fourth embodiment of this invention.

Components whose configuration is identical to that of corresponding parts of the first embodiment are labeled with the same numbers. The order of operations and the internal configuration are also identical to those of the first embodiment.

Case 46 of device 45 has the form of a card.

Display 4 and input key array 3 are in the lower portion of the center of front surface 46a of device 45. On either side of the lower portion of surface 46a are tongue-shaped measurement electrodes 47 and 48. Parallelogram-shaped current electrodes 49 and 50 are on either side of the upper portion of surface 46a. Flanges 51 and 52 protrude from either side on the upper portion of device 45.

When the user grasps the sides of device 45 from the front, the parts of the hands between the index fingers and the thumbs come up against the bottoms of flanges 51 and 52 so as to position the hands properly. When he extends the thumbs upward along surface 46a, the portions of the palms between the bases of the index fingers and the wrists make contact with measurement electrodes 47 and 48, and the pads of the thumbs make contact with current electrodes 49 and 50.

Because both current electrodes 49 and 50 and measurement electrodes 47 and 48 are placed on the front of the device, the device can be made thinner and lighter. And because the case is easier to mold, the device costs less to make than those of the prior art. With this design it is best that the user bend the thumbs at the first joint and place them on the edge where front surface 46a meets top surface 46b in order to position the hands correctly. The portions of the thumbs between the first and second joints will then be in contact with current electrodes 49 and 50.

Figure 7:
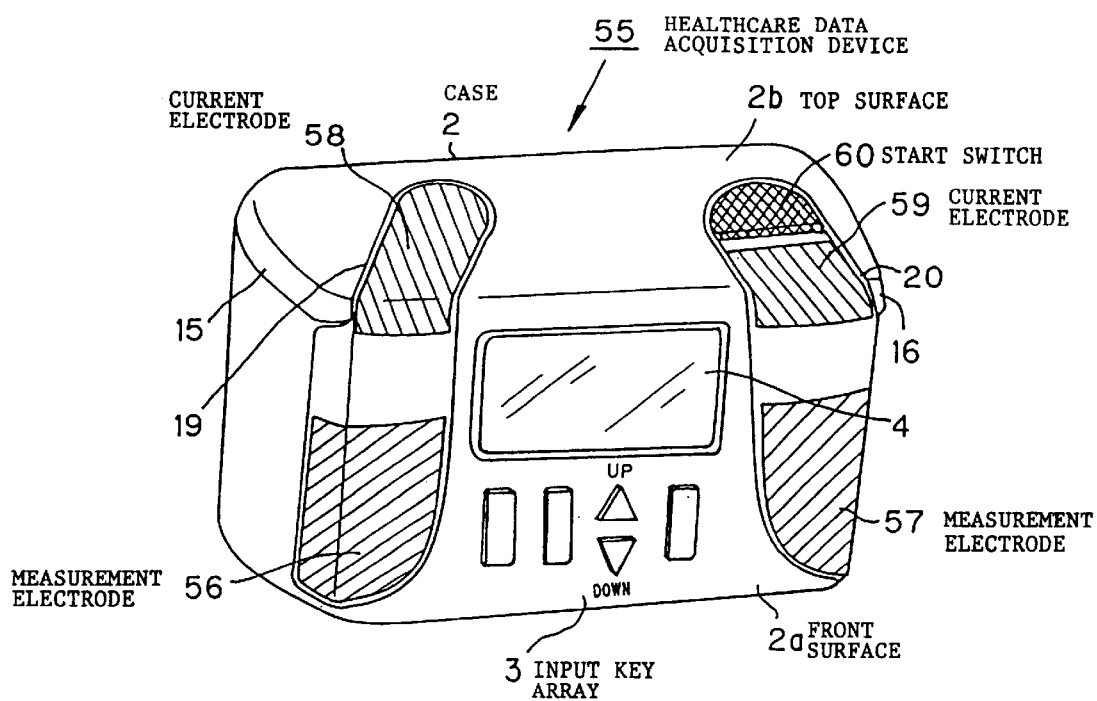
FIG. 7 is a perspective drawing of a healthcare data acquisition device in accordance with the fifth embodiment of this invention.

FIG. 7 shows healthcare data acquisition device 55, the fifth embodiment of this invention. Components whose configuration is identical to that of corresponding parts of the first embodiment are labeled with the same numbers. The order of operations and the internal configuration are also identical to those of the first embodiment.

In this embodiment, tongue-shaped current electrode 58 on the left side of device 55 extends slightly from top surface 2b onto front surface 2a. Around current electrode 58 and measurement electrode 56 is outline 19, which guides the position of the left hand. On the right side of top surface 2b, extending slightly from surface 2b to surface 2a, is current electrode 59. The end portion of current electrode 59 on surface 2b is cut away, leaving the electrode rectangular in shape. In the cut-away portion is semicircular start switch 60. Outline 20, which guides the position of the right hand, encloses start switch 60, current electrode 59 and measurement electrode 57.

When the user grasps device 55 with both hands in the locations outlined by guidelines 19 and 20, the portions of the palms between the bases of the index fingers and the wrists come in contact with measurement electrodes 56 and 57. The pad of the left thumb from the tip to between the first and second joints is in contact with current electrode 58. The pad of the right thumb is in contact with start switch 60, and the portion of that thumb between the first and second joints is in contact with current electrode 59.

As can be seen, start switch 60 is placed in the location which corresponds to the tip of the thumb. When the hands are in contact with electrodes 56, 57, 58 and 59 and all preparations for measurement have been completed, the user can touch start switch 60 without moving the hand or even the finger. This design prevents measurement errors due to the measurement starting just after the user has moved the finger to actuate the start switch. That is, if the start switch is in a separate location, the hand might not be touching both electrodes properly even though it was positioned correctly at the start. Placing the start switch under the thumb provides a highly accurate measurement. The start switch need not be shaped like a semicircle, as shown in the drawing. It would also be possible to place the sort of start switch used in prior art devices in the location corresponding to the tip of the right thumb.

Figure 8A:
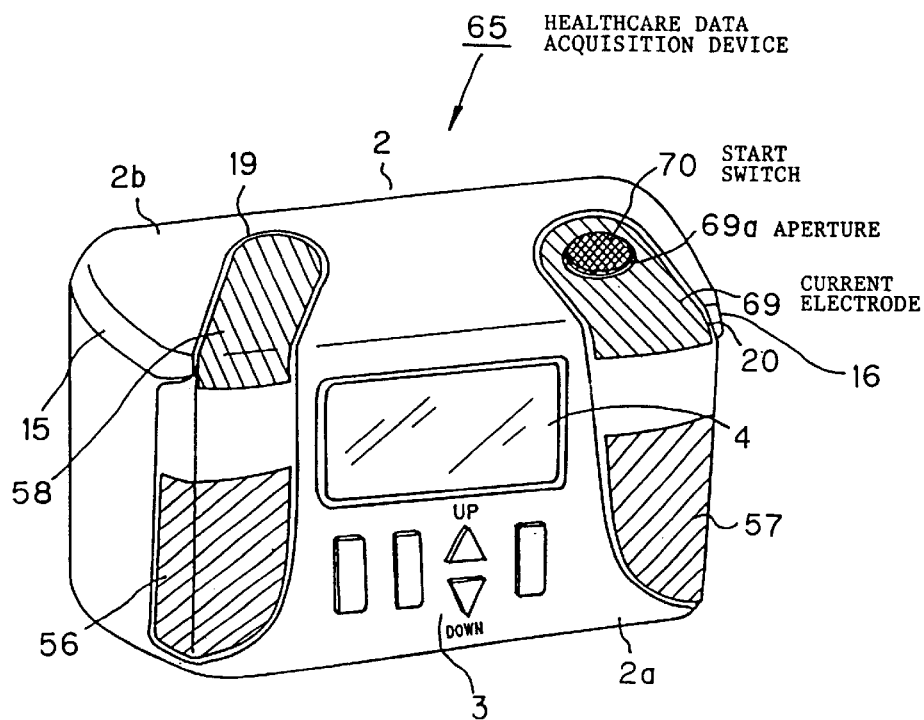
FIG. 8(a) is a perspective drawing of a healthcare data acquisition device in accordance with the sixth embodiment of this invention.

FIG. 8(a) shows healthcare data acquisition device 65, the sixth embodiment of this invention.

Components whose configuration is identical to that of corresponding parts of the first and fifth embodiments are labeled with the same numbers. The order of operations and the internal configuration are also identical to those of the first and fifth embodiments.

In this embodiment, tongue-shaped current electrodes 58 and 69 are located on either side of top surface 2b of device 65 and extend slightly over onto front surface 2a. Outlines 19 and 20 are provided around the peripheries of current electrodes 58 and 69 and measurement electrodes 56 and 57 to guide the placement of the hands. A portion of the end of current electrode 69 is cut away to form aperture 69a, in which round-shaped start switch 70 is seated.

When the user grasps device 65 with both hands in the locations outlined by 19 and 20, the portions of the palms between the bases of the index fingers and the wrists come in contact with measurement electrodes 56 and 57. The pad of the left thumb from the tip to between the first and second joints is in contact with current electrode 58. The center of the pad of the right thumb is in contact with start switch 70, and the portion of that thumb from the periphery of the switch to between the first and second joints is in contact with current electrode 69.

As can be seen, start switch 70 is placed in the center of current electrode 69 near the tip of the thumb. When the hands are in contact with electrodes 56, 57, 58 and 69 and all preparations for measurement have been completed, the user can touch start switch 70 without moving his hand or even his finger. This design prevents measurement errors due to the measurement starting just after the user has moved his finger to actuate the start switch. That is, if the start switch is in a separate location, the hand might not be touching both electrodes properly even though it was positioned correctly at the start. Placing the start switch under the thumb provides a highly accurate measurement.

Figure 8B:
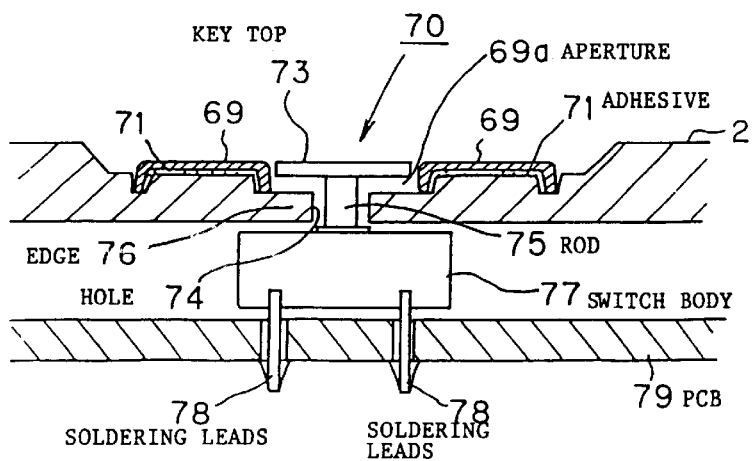
FIG. 8(b) is a cross section of the area around the start switch in the healthcare data acquisition device in accordance with the sixth embodiment of this invention.

FIG. 8(b) is a rough cross section of the area around start switch 70. Current electrode 69, which consists of an SUS sheet, is fixed to case 2 by means of adhesive 71. An opening is made in both electrode 69 and case 2, and in this aperture 69a is inlaid key top 73 of start switch 70, a mechanical key switch. Placing the surface of flat key top 73 level with or slightly lower than the surrounding electrode 69 will prevent it from being actuated accidentally. Rod 75 is inserted into hole 74 in case 2. The diameter of hole 74 is smaller than that of aperture 69a in electrode 69, so the edge 76 of hole 74 serves as a stop for key top 73. When the switch body 77 of the start switch is fixed to printed circuit board 79 in case 2 by soldering leads 78, the switch is connected to board 79. The start switch, however, need not be configured in this particular way.

Figure 9:
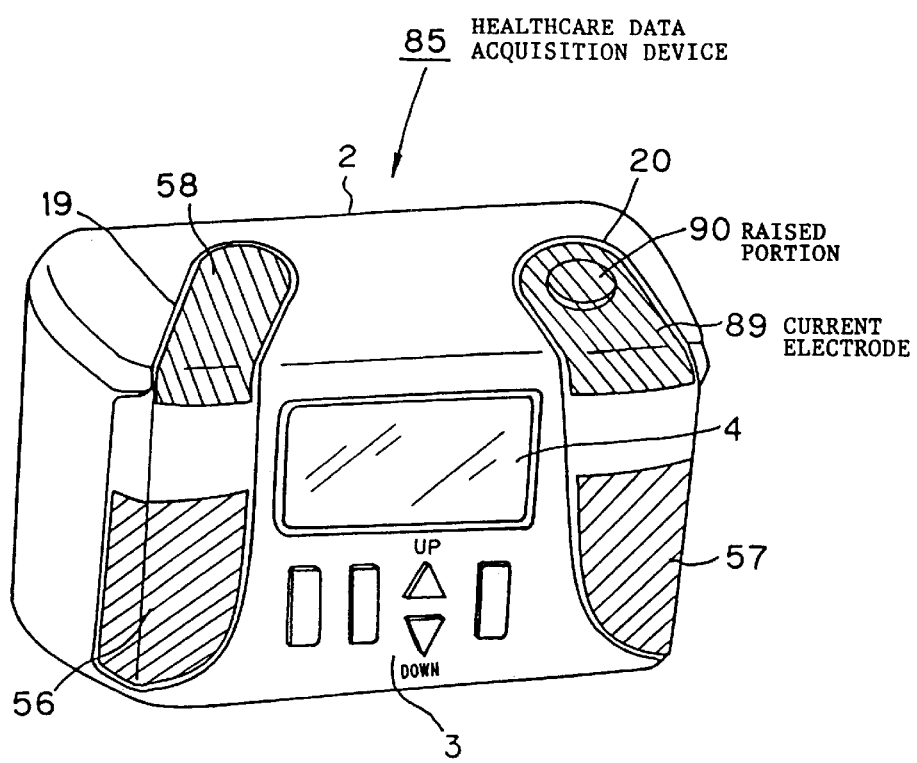
FIG. 9 is a perspective drawing of a healthcare data acquisition device in accordance with the seventh embodiment of this invention.

FIG. 9 shows healthcare data acquisition device 85, the seventh embodiment of this invention. With the exception of current electrode 89, all components are configured just as in the fifth and sixth embodiments, so they will not be further discussed in this section.

Figure 10A:
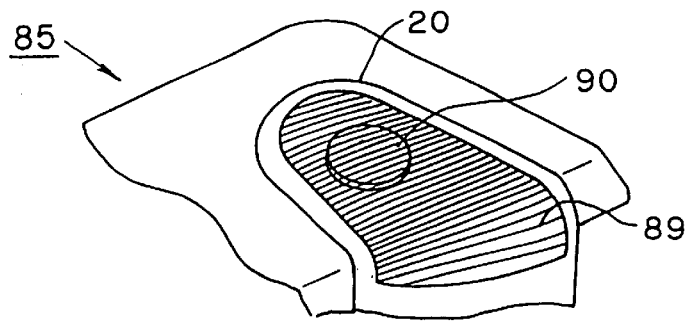
FIG. 10(a) is a magnified view of the area around the current electrode in the healthcare data acquisition device in accordance with the seventh embodiment of this invention.

In this embodiment, the start switch is formed integrally with current electrode 89. As can be seen in the blow-up of current electrode 89 in FIG. 10(a), there is a round raised portion 90 in the part of electrode 89 where the tip of the thumb goes. A start switch which is integral to the electrode is provided in this raised portion 90.

Figure 10B:
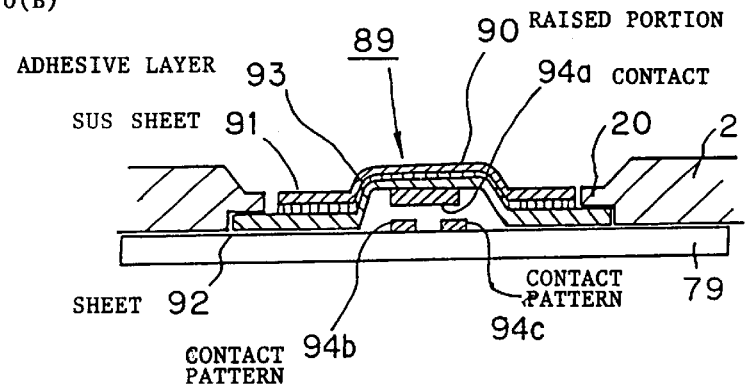
FIG. 10(b) is a cross section of the raised portion of the same current electrode.

FIG. 10(b) is a rough cross section of raised portion 90, in which current electrode 89 is formed by embossing SUS sheet 91. The interior of portion 90 forms a hollow chamber. To provide insulation, a silicon resin sheet 92 is interposed between current electrode 89 and printed circuit board 79. Sheet 92 is fixed to current electrode 89 by adhesive layer 93. On the interior of raised portion 90, there is a chamber formed between sheet 92, which is fixed to the underside of the electrode, and printed circuit board 79. On the underside of the raised portion of resin sheet 92 is contact 94a, which is made of a conductive print, resin or gum of carbon or some similar material. On printed circuit board 79, facing contact 94, contact patterns 94b and 94c are formed from copper foil or created by a metal plating process. Sheet 92 is fixed to case 2 or printed circuit board 79. Sheet 92 should be able to insulate printed circuit board 79 from SUS sheet 91, so it should be made of polyethylene, nylon, or some similar material.

When the user grasps device 85 with the hands in outlines 19 and 20, the portion of the right thumb from the tip to the second joint is in contact with current electrode 89. The pad of the right thumb is in contact with raised portion 90 (i.e., with the start switch). When he presses portion 90 with the pad of the thumb, it goes down, and the path between contact patterns 94b and 94c is shorted by contact 94a. This is used as the contact signal for the start switch.

If the start switch is formed integrally with current electrode 89 in this way, when the hands are in contact with electrodes 56, 57, 58 and 89 and all preparations for measurement have been completed, the user can touch the start switch without moving the hand or even the finger. This design prevents measurement errors which occur when the hands are positioned correctly but the measurement begins just after the user moves the finger to actuate the start switch. With this configuration, the hands are in contact with electrodes 56, 57, 58 and 89 when the measurement commences, enabling a highly accurate measurement.

Figure 11:
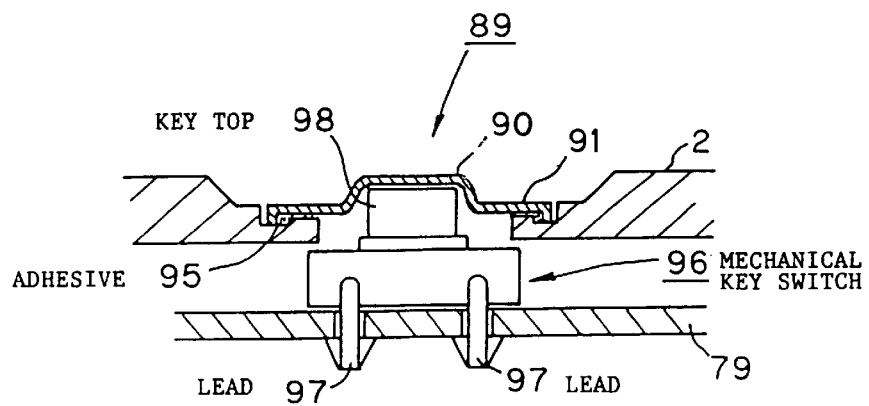
FIG. 11 is a cross section of the start switch in the healthcare data acquisition device in accordance with the eighth embodiment of this invention.

FIG. 11 is a cross section of the start switch in a healthcare data acquisition device which is the eighth embodiment of this invention. With the exception of current electrode 89, the configuration of the components is just as in the seventh embodiment. Corresponding parts are labeled with the same numbers and are not further discussed in this section.

In this embodiment, mechanical key switch 96 serves as the start switch. Current electrode 89 is formed from an SUS sheet 91 on which a raised portion 90 has been embossed. Electrode 89 is fixed to case 2 by adhesive 95. The leads 97 for key switch 96 are soldered and electrically connected to printed circuit board 79, which is inside case 2. Key top 98 of switch 96, which is made of an insulating resin, is enclosed in the hollow chamber under the raised portion 90 of current electrode 89.

When the user places the hands in the proper positions, the pad of the right thumb is in contact with raised portion 90 (i.e., with the start switch). When all preparations for measurement have been completed, the user presses raised portion 90 with the right thumb. Portion 90 goes down, and key top 98 is depressed. A start signal is transmitted to measurement and operation control unit 22 (see FIG. 2).

If the start switch is formed integrally with current electrode 89 in this way, when the hands are in contact with electrodes 56, 57, 58 and 89 and all preparations for measurement have been completed, the user can touch the start switch without moving the hand or even the finger. This design prevents measurement errors which occur when the hands are positioned correctly but the measurement begins just after the user moves the finger to actuate the start switch. With this configuration, the hands are in contact with electrodes 56, 57, 58 and 89 when the measurement commences, enabling a highly accurate measurement.

Figure 12A:
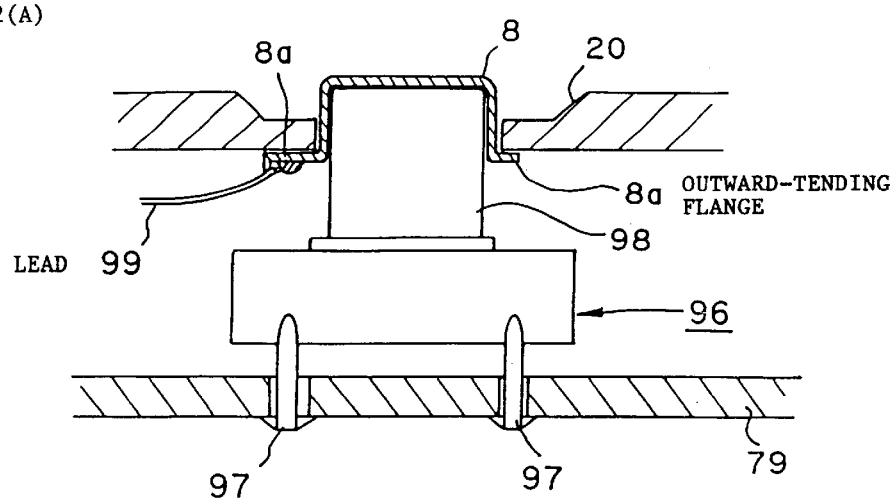
FIG. 12(a) is a cross section of the start switch in the healthcare data acquisition device in accordance with the ninth embodiment of this invention.

FIG. 12(a) shows a rough sketch of a start switch in a healthcare data acquisition device which is the ninth embodiment of this invention.

In this embodiment, too, the start switch is a mechanical key switch 96 which is integral to one of the electrodes. Here, however, the head of key top 98 serves as the current electrode. In other words, current electrode 8 in the healthcare data acquisition device shown in FIG. 1(a) is itself the start switch. The rest of the configuration is just as in the first embodiment, so it shall not be further discussed at this point.

To form current electrode 8, a thin plate of SUS or some similar material is pressed into the shape of a cylinder with a bottom. Cylindrical key top 98 of mechanical key switch 96 is formed from an insulating resin or some similar material. The upper portion of key top 98 is inserted into the cavity in current electrode 8 and fixed to the electrode with an adhesive. On the edges surrounding the cavity in electrode 8 are outward-tending flanges 8a. When key top 98 returns from being pressed, these flanges come up against the inner surface of the edge of the opening in case 2, which acts as a stop. A lead wire 99 for current may also be soldered to one of flanges 8a. When leads 97 of mechanical key switch 96 are soldered to printed circuit board 79 in case 2, the switch is fixed in place and electrically connected.

The user places the tip of the thumb in contact with current electrode 8. When all preparations for measurement have been completed, he depresses current electrode 8, which is attached to key top 98. This causes a start signal to be transmitted to measurement and operation control unit 22.

If the start switch is formed integrally with current electrode 8 in this way, when the hands are in contact with electrodes 5, 6, 7, and 8 and all preparations for measurement have been completed, then the user can touch the start switch without moving the hand or even the finger. This design prevents measurement errors which occur when the hands are positioned correctly but the measurement begins just after the user moves the finger to actuate the start switch. With this configuration, the hands are in contact with the electrodes when the measurement commences, enabling a more accurate measurement.

Figure 12B:
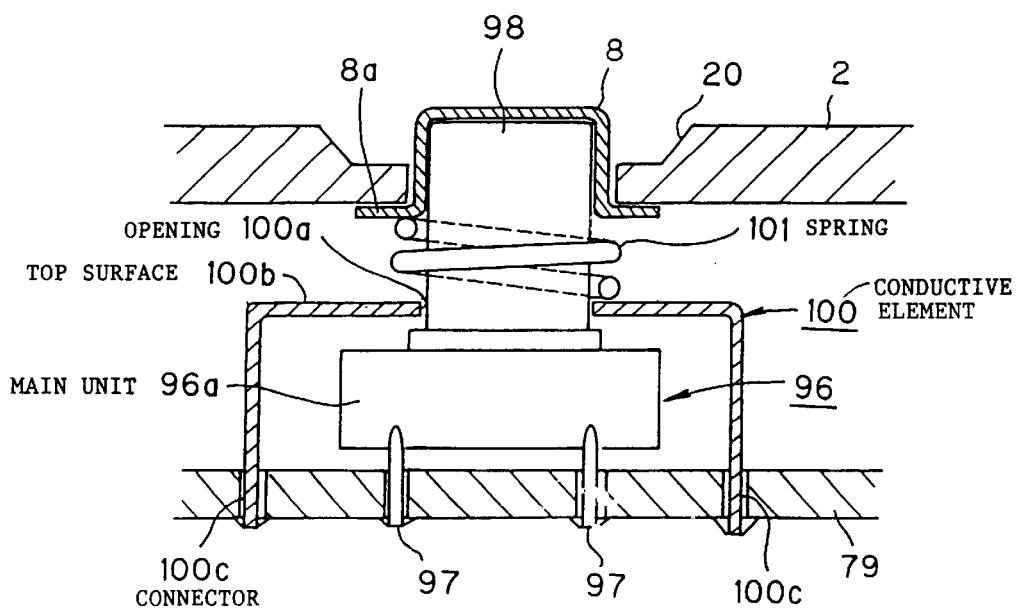
FIG. 12(b) is a cross section of a modified version of the start switch in the healthcare data acquisition device in accordance with the ninth embodiment of this invention.

Supplying current to the electrode via lead wire 99 is not the only possible design. As can be seen in FIG. 12(b), current electrode 8 and printed circuit board 79 may alternatively be connected by means of conductive elements.

Conductive element 100, a closed cylinder made of a thin plate of iron or copper, is placed on the exterior of main unit 96a of key switch 96. Spring 101, which is made of a conductive material, is placed around key top 98, which protrudes through opening 100a in the conductive element. Spring 101 is sandwiched between flanges 8a on current electrode 8 and top surface 100b of conductive element 100. Connector 100c of element 100 is soldered to printed circuit board 79 to immobilize the element and connect it electrically. Thus current electrode 8 is always electrically connected to printed circuit board 79 through spring 101 regardless of the operational state of key switch 96.

Figure 13:
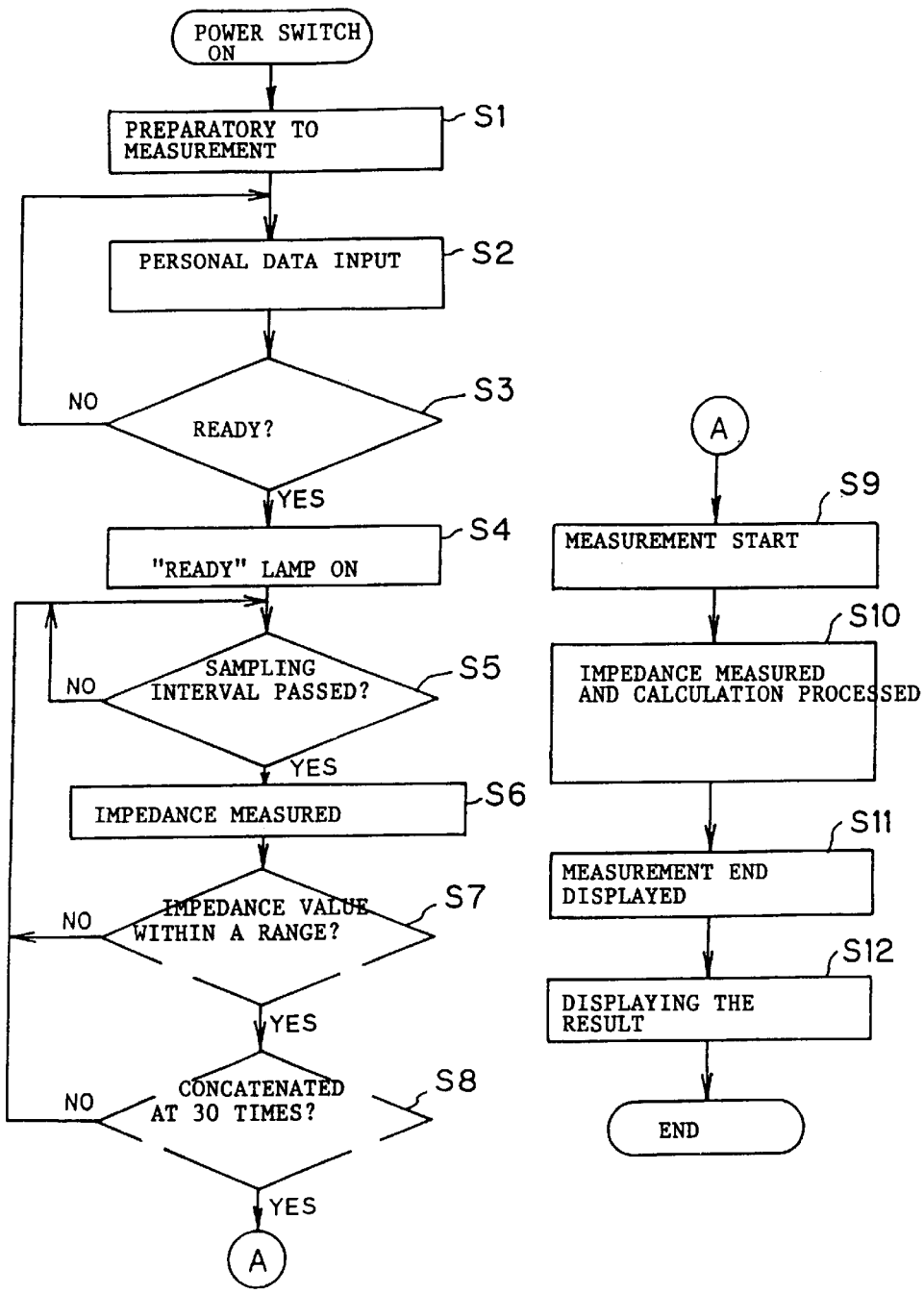
FIG. 13 is a flowchart of the measurement process executed by the healthcare data acquisition device in accordance with the tenth embodiment of this invention.

FIG. 13 is a flowchart of the measurement process executed by the healthcare data acquisition device which is the tenth embodiment of this invention. The actual configuration of this embodiment of the healthcare data acquisition device is identical to those of the first through fourth embodiments. In this embodiment, when power switch 9 is turned on, various processing are executed by a specified program in measurement and operation control unit 22. There is no start switch; the measurement begins automatically and is fully executed. The measurement process is explained with reference to the flowchart in FIG. 13.

When power switch 9 is turned on, various processes are executed in preparation of measurement, such as initializing the RAM and checking every circuit element and display element (Step 1).

Next, the patient enters via key input unit 3 personal data, such as height, weight, age and sex (Step 2).

A judgment is made as to whether the entry of these data has been completed (Step 3).

If the answer in Step 3 was "no," then return to Step 2 and stand by for the personal data to be entered. At this time a prompt to enter the data may be shown on display 4. If the answer in Step 3 was "yes," the word "Ready" appears on display 4 (Step 4). A "Ready" display lamp could alternatively be provided independently of display 4.

The user places both hands in the specified positions. The pads of the thumbs are in contact with the current electrodes and the portions of the palms from the bases of the index fingers to the wrists are in contact with the measurement electrodes.

Next, a judgment is made as to whether a sampling interval has been passed (for example, ⅟100 sec) (Step 5).

If the answer in Step 5 was "no," then the sampling interval is in waiting status. If the answer in Step 5 was "yes," then the impedance is measured between the two measurement electrodes touching the hands (Step 6).

A judgment is made as to whether the impedance value obtained falls within the range specified for the body (for example, 350 to 1,500S) (Step 7).

If the answer in Step 7 was "no," then return to Step 5. If it was "yes," then the impedance value obtained is concatenated at least a given number of times (say, 30) and a judgment is then made as to whether the new value falls within the expected range of the impedance of the body (Step 8).

If the answer in Step 8 was "no," then return to Step 5. If the answer in Step 8 was "yes," then it is assumed that the hands are in proper contact with the current and measurement electrodes, and a message that measurement has begun appears on display 4 (Step 9). Alternatively, such a message may be conveyed by the flashing of a light which is independent of display 4.

The impedance between the hands is then measured and specified calculations are processed (Step 10).

When the measurement has been completed, a message to that effect appears on display 4 (Step 11).

Finally, the result of the measurement and useful advice with respect to healthcare management appear on display 4 (Step 12), and the series of measurement operations is completed.

When power switch 9 is turned on, the device determines whether the hands are in proper contact with the current and measurement electrodes. There is no start switch to actuate; the measurement begins automatically. This design prevents measurement errors which occur when the hands are positioned correctly but the measurement begins just after the user moves the finger to actuate the start switch. With this configuration, the hands are in contact with the electrodes when the measurement commences, enabling a more accurate measurement.

Figure 14A:
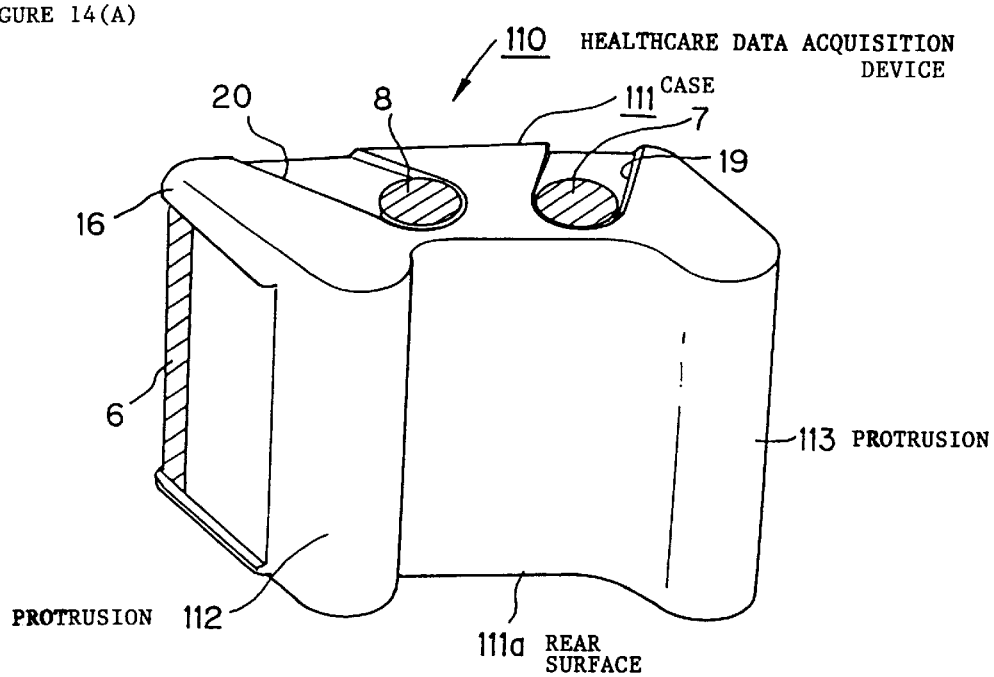
FIG. 14(a) is a rear view of the healthcare data acquisition device in accordance with the eleventh embodiment of this invention.
Figure 14B:
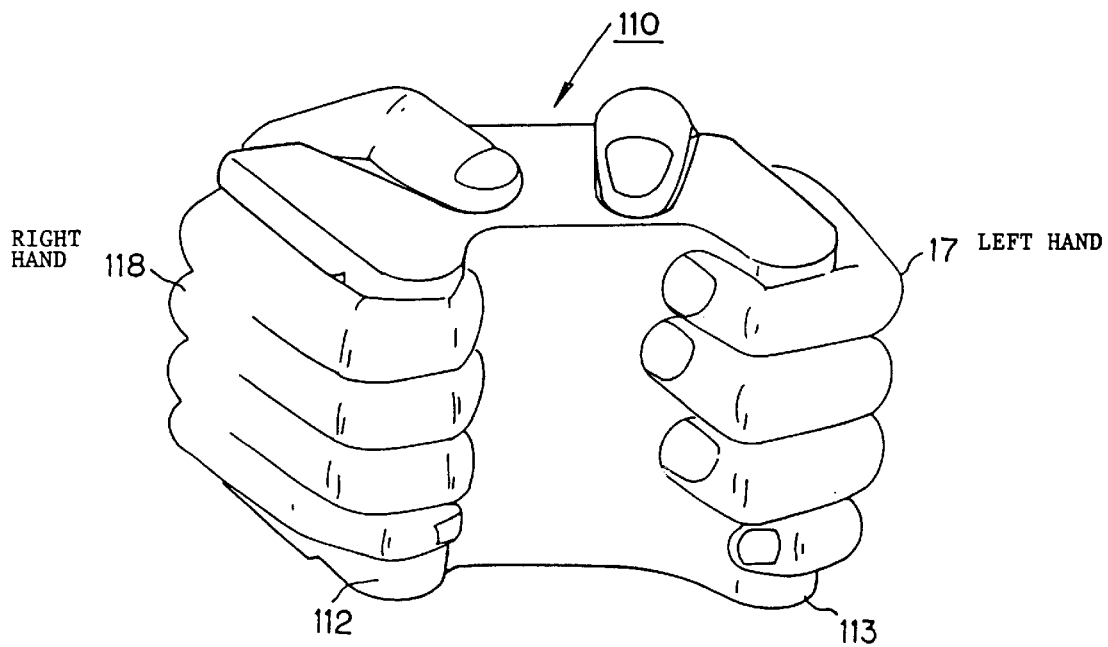
FIG. 14(b) illustrates the use of the healthcare data acquisition device in accordance with the eleventh embodiment of this invention.

FIG. 14(*a*) shows a rear view of the exterior of healthcare data acquisition device 110, the eleventh embodiment of this invention.

With the exception of rear surface 111*a*, device 110 has the same configuration as healthcare data acquisition device 1 in the first embodiment. Corresponding parts are labeled with the same numbers. On either side of rear surface 111*a* of case 111 are protrusions 112 and 113, which extend in the vertical direction. Protrusions 112 and 113 project backward along the sides of the case. They curve into half-cylinders which gradually curve into rear surface 111*a*. When the patient grasps device 110 within outlines 19 and 20, as can be seen in FIG. 14 (*b*), the index through least fingers bend around protrusions 112 and 113. The fingertips exert pressure on protrusions 112 and 113 and keep the fingers in the proper position on rear surface 111*a*.

Figure 15:
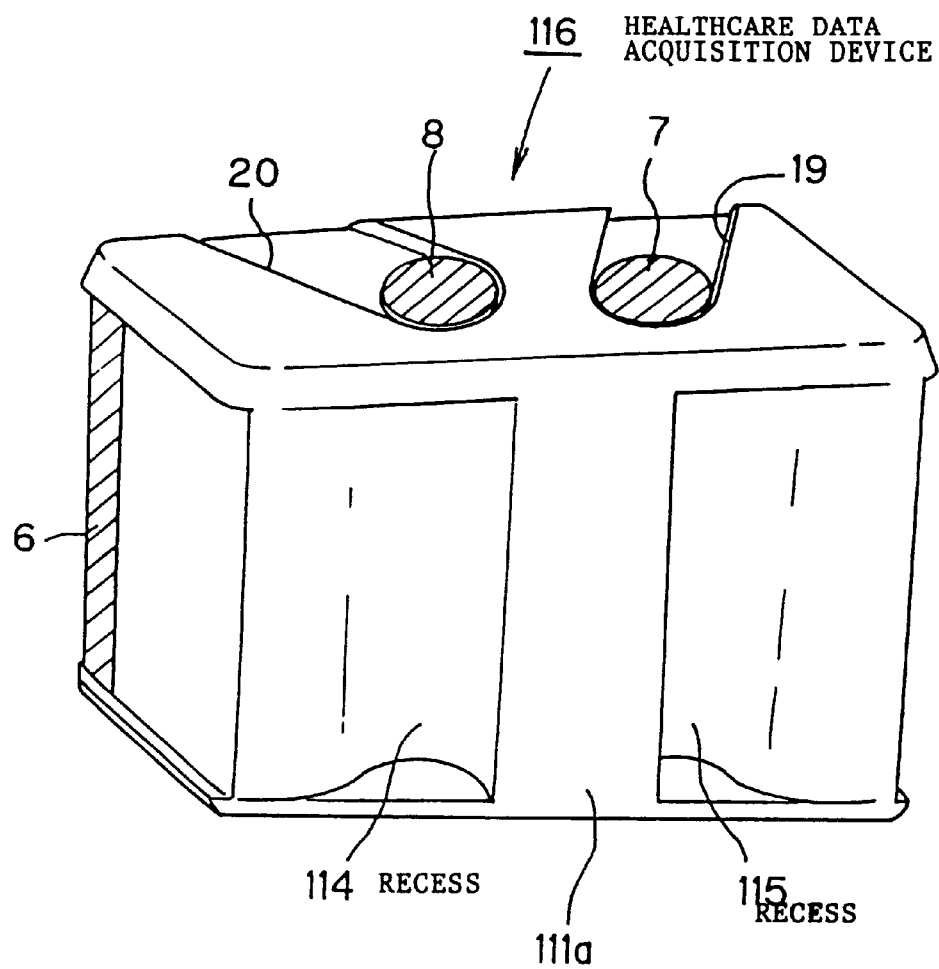
FIG. 15 is a rear view of the healthcare data acquisition device in accordance with the eleventh embodiment of this invention.
Figure 16:
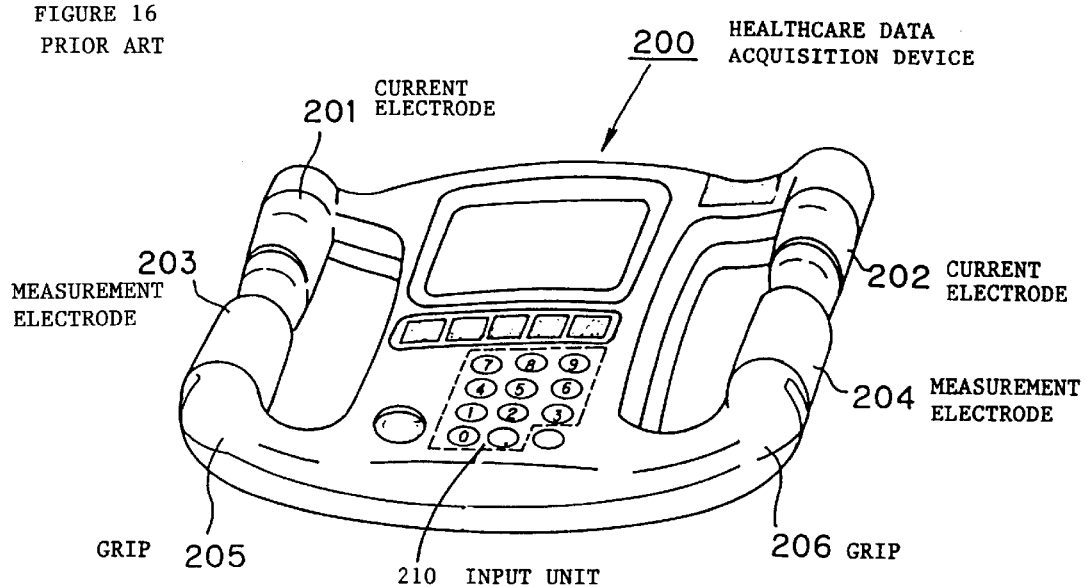
FIG. 16 is a healthcare data acquisition device of the prior art.
Figure 17:
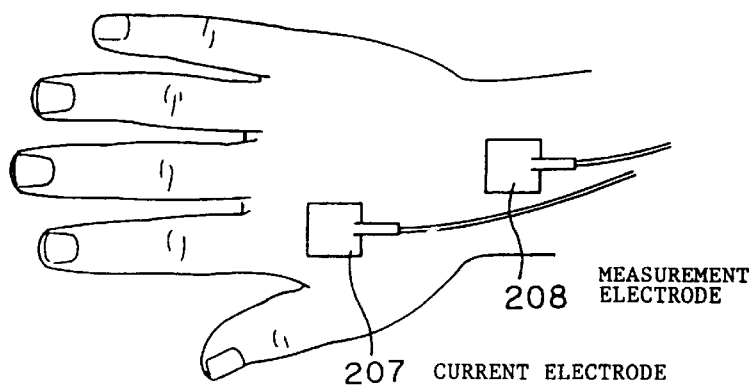
FIG. 17 illustrates the basic measurement method used to measure impedance in the prior art.

FIG. 15 shows healthcare data acquisition device 116, which keeps the fingers in the proper position by means of indentations 114 and 115 on rear surface 111*a* rather than by protrusions. With the exception of the configuration of the rear surface, device 116 is identical to healthcare data acquisition device 110 of the eleventh embodiment. Corresponding parts are labeled with the same numbers and are not further discussed in this section.

From either side, rear surface 111*a* curves inward gradually toward its center, forming half-cylinders. Toward the center, the surface curves outward again to meet flat surface 111*a*. Indentations 114 and 115 function in the same way as protrusions 112 and 113. When the patient grasps device 116 within outlines 19 and 20, the index through least fingers bend around the curving surfaces of indentations 114 and 115. This keeps them in the proper position on rear surface 111*a*. Along with outlines 19 and 20, protrusions 112 and 113 and indentations 114 and 115 constitute the position guides, which are not limited to protrusions or indentations. They may be shaped in some other way or they may consist of lines or shapes painted on the case to indicate where to place the fingertips.

According to the invention, by applying current only to the thumbs, which are the thickest digits and so have a low resistance value, errors related to the constant current source are minimized and a highly accurate impedance measurement is achieved. Moreover, since the thumbs are independent both structurally and functionally from the other four fingers, applying current only to the thumbs eliminates the possibility that the current path will vary. It is then possible to measure the impedance with good accuracy and repeatability. The area of the skin where the current electrodes make contact with the thumbs is large enough to allow the use of smaller electrodes. This in turn enables the entire device to be made smaller, lighter and cheaper. If the current is to be applied to the pads of the thumbs, then, the electrodes can be installed on the surface of the device. The patient need only place the thumbs on them or grasp them, and the impedance can easily be measured.

These position guides guarantee that the specified parts of the thumbs make proper contact with the current electrodes and thus provide a healthcare data acquisition device capable of a high degree of accuracy and repeatability. The thumbs may also be positioned correctly by using current electrodes which are designed so as to maintain contact with the specified parts of the thumbs. Another possibility is to provide a structural component along the periphery of each electrode to limit the movement of the thumb and guide its placement. This design makes it easier to position the specified portions of the thumbs on the current electrodes. It thus makes it possible to provide a healthcare data acquisition device capable of high accuracy and repeatability.

The current electrodes may be three-dimensional and conform to the contours of the specified portions of the thumbs, or they may be flat but shaped in such a way that the user can confirm that the thumbs are in contact with the electrodes.

Although the thumbs are selected as the sites where the current is to be applied, they are not far from where the electrodes were attached in the prior art measurement method. The "site where the voltage will be measured" refers to the portion of the body where the electrode to measure voltage must be in contact with the skin. The deviation of the current from the main current path is also slight, so the problems of measurement error and the incongruity of the measurement method with respect to the prior art method are minimized. A healthcare data acquisition device can be produced which is capable of highly accurate measurements. Because the current and measurement electrodes can be placed quite close to each other, this allows the device to be made smaller, lighter and cheaper. If the voltage is measured between the base of the thumb and the wrist on each hand, then the impedance can be easily measured if the patient places the hands on or grasps measurement electrodes which are installed on the surface of the device.

With this design, the specified parts of the body are placed in contact with the current and measurement electrodes and preparations are made to perform the measurement. The measurement then begins without any change in the state of contact. There is no danger of the sort of measurement error which might occur if there were, for example, a switch in a separate location which must be actuated to begin the measurement, so that the measurement might be performed with the fingers in the wrong position. The present design insures a highly accurate measurement.

Preparations for the measurement are completed while the specified body parts are in contact with the current electrodes. The patient can actuate the start switch without breaking contact with the electrodes. This prevents the sort of measurement errors which are associated with initiating the measurement operation and so insures that a highly accurate measurement can be made. Thus when the current electrodes have been placed in contact with the specified part of the body and the preparation has been completed, no change in the state of contact is required to begin the measurement. This prevents the sort of measurement errors which are associated with initiating the measurement operation and so insures that a highly accurate measurement can be made.

What is claimed is:

1. A healthcare data acquisition device, comprising:
   a pair of current electrodes configured to contact substantially only thumbs of a user for applying a current to said user;
   a pair of measurement electrodes configured to contact a pair of specified portions of palms of said user for measuring a voltage between said pair of specified portions, said voltage being generated by said current applied by said current electrodes; and
   a computation and control unit for calculating an impedance between said pair of specified portions based on said applied current and said measured voltage, and for processing said calculated impedance to obtain a healthcare data of said user.

2. A healthcare data acquisition device according to claim 1, further comprising a pair of thumb position guides to insure that said thumbs of the user make contact with said pair of current electrodes.

3. A healthcare data acquisition device according to claim 1, wherein said current electrodes are shaped corresponding to left and right thumbs of said user.

4. A healthcare data acquisition device according to claim 1, wherein said pair of specified portions of said user's palm to be measured are respectively located between left and right thumbs and wrists of said user.

5. A healthcare data acquisition device according to claim 1, wherein measurement of said voltage for calculating said impedance begins when said contact between said current electrodes and thumbs and said contact between said measurement electrodes and said specified portions are respectively maintained in a state of contact.

6. A healthcare data acquisition device according to claim 5, further comprising a start switch which is provided in a cut-away portion of at least one of said current electrodes.

7. A healthcare data acquisition device according to claim 5, further comprising a start switch which is formed integrally with at least one of said current electrodes.

8. A healthcare data acquisition device according to claim 5, wherein said measurement of said voltage for calculating said impedance automatically begins when said contact between said current electrodes and thumbs and said contact between said measurement electrodes and said specified portions are respectively maintained in said state of contact and said state of contact is confirmed.

* * * * *